United States Patent [19]

Bellasio et al.

[11] 4,075,241
[45] Feb. 21, 1978

[54] 2-(ARYL)-3-(DIMETHYLAMINO)BUTYL-3,4,5-TRIMETHOXYBENZOATES

[75] Inventors: Elvio Bellasio, Albate (Como); Franco Cristiani, Pavia, both of Italy

[73] Assignee: Gruppo Lepetit S.p.A., Milan, Italy

[21] Appl. No.: 251,025

[22] Filed: May 8, 1972

[30] Foreign Application Priority Data

May 12, 1971 Italy .................................. 24390/71

[51] Int. Cl.$^2$ ............................................. C07C 65/08
[52] U.S. Cl. ....................................... 560/73; 560/39;
560/32; 560/100; 260/570.6; 424/300; 424/308;
424/330; 560/104; 560/55; 560/38; 560/107;
560/106
[58] Field of Search .......................... 260/570.6, 473 R

[56] References Cited

U.S. PATENT DOCUMENTS

| | | | |
|---|---|---|---|
| 2,538,792 | 6/1951 | Moersch | 260/570.6 |
| 2,556,868 | 6/1951 | Carter et al. | 260/570.6 |
| 2,958,697 | 11/1960 | Shapiro et al. | 260/473 R |
| 2,971,018 | 2/1961 | Shapiro et al. | 260/473 R |
| 2,983,755 | 5/1961 | Kollonitsch et al. | 260/570.6 |
| 3,409,672 | 11/1968 | Trepanier | 260/570.6 |
| 3,562,262 | 2/1971 | Schmidt et al. | 260/473 R |
| 3,714,229 | 1/1973 | Saari et al. | 260/473 R |

FOREIGN PATENT DOCUMENTS 2,369M  10/1962  France ............................. 260/473 R

OTHER PUBLICATIONS

Burger, Medicinal Chemistry, Wiley Interscience (1970) pp. 64, 71, 72.

March, Advanced Organic Chemistry, McGraw-Hill Co. (1968) pp. 589, 891, 319–320, 663.
Morsch, Monatsh, 61 299–313; C.A. 27 713.

Primary Examiner—Richard L. Raymond
Attorney, Agent, or Firm—Theodore Post; Daniel L. De Joseph

[57] ABSTRACT

The compounds 2-Aryl-3-amino-1-butanol derivatives of the formula

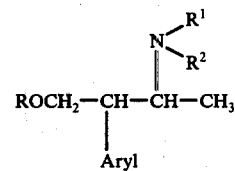

wherein R represents hydrogen or acyl; $R^1$ and $R^2$ each independently represents hydrogen, phenyl lower alkyl, or lower alkoxy substituted phenyl lower alkyl, or both $R^1$ and $R^2$ are lower alkyl; and their pharmaceutically acceptable acid salts.

The compounds are crystalline solids or liquids which, having two asymmetry centers, can be obtained in their stereoisomeric forms as racemic mixtures or in their optically active forms. The compounds have cardiovascular activity as coronary dilators.

The compounds can be prepared by reacting an α-arylcrotonate with ammonia or with an amine followed by hydrogenation of the carbalkoxy group to give the corresponding butanol. The butanols are acylated in usual ways to give the compounds of formula (I) wherein R represents an acyl group.

2 Claims, No Drawings

2-(ARYL)-3-(DIMETHYLAMINO)BUTYL-3,4,5-TRIMETHOXYBENZOATES

SUMMARY OF THE INVENTION

This invention is concerned with 2-Aryl-3-amino-1-butanol derivatives represented by the formula

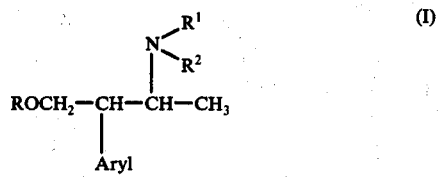

wherein R represents hydrogen or acyl; $R^1$ and $R^2$ each independently represents hydrogen, phenyl lower alkyl or lower alkoxy-substituted phenyl lower alkyl or both are lower alkyl groups; and their pharmaceutically acceptable acid salts. The term "acyl" as used in the specification and in the claims refers to cinnamoyl, lower alkyl-substituted phenacetyl, lower alkoxy-substituted benzoyl and phenylcarbamyl groups; the terms "lower alkyl" and "lower alkoxy" refer to one to four carbon alkyl and alkoxy groups; and the term "Aryl" refers to phenyl, naphthyl and substituted phenyl wherein the substituents are selected from halo, i.e., chloro and bromo, and lower alkoxy.

The compounds of the invention are crystalline solids or liquids which, having two asymmetry centers, can be obtained in their stereoisomeric forms as racemic mixtures or as optically active compounds. The compounds exhibit cardiovascular system activity, particularly as coronary dilators and/or β-blockers. Their activity is associated with low toxicities. A preferred group of compounds comprises those compounds of formula (I) wherein the Aryl is a halo- or lower alkoxy-substituted phenyl or a naphthyl group, R is a lower alkoxy-substituted benzoyl, a cinnamoyl or a phenylcarbamyl group and $R^1$ and $R^2$ are methyl groups.

The compounds of the invention can be prepared by reaction of an α-arylcrotonate with ammonia or with a suitable amine followed by hydrogenation of the carbalkoxy group to the primary alcohol according to the following scheme:

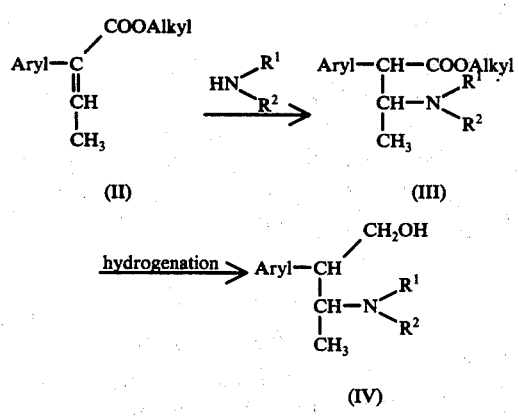

In the preparative procedures, substantially one molecular proportion of an α-arylcrotonate dissolved in an organic solvent which is preferably selected from the one to four carbon water-miscible alkanols is treated with a large excess of ammonia or with a mono- or di-substituted amine, which, when the substituents are lower alkyl, may conveniently be dissolved in water. The reaction mixture is allowed to stand under agitation for a period of time which, depending on the temperature or pressure, may vary from about 5 hours to 24 hours or more. The preferred temperature ranges from about room temperature to about 50° to about 60° C. At room temperature, the reaction is generally carried out at atmospheric pressure while at an elevated temperature superatmospheric pressure may be required. In the latter case, the reaction is conveniently carried out in a closed vessel under 10 to 30 atmospheres of nitrogen.

The reaction product is then recovered, and may be transformed into a suitable acid salt for ready purification. The crude free aminoester may be utilized as such for the hydrogenation step. For this purpose the compound is treated in an inert organic solvent with a large excess of a mixed metal hydride which preferably is lithium aluminum hydride. The recovered 2-Aryl-3-substituted amino-1-butanol is then acylated according to procedures which are familiar to all organic chemists.

With the addition of an amine to the double bond of the α-arylcrotonate of formula (II), two stereoisomeric forms of the aminobutyrate of formula (III) are obtained. The proportionate ratio of these stereoisomeric forms may vary, depending upon several factors which essentially are the cis- or trans- form of the starting crotonate or their proportionate ratio, the nature of the Aryl substituent and the reaction conditions.

The separation of the stereoisomers and their optically active components may be effected after formation of the aminobutyrate, although in some particular cases it is preferably carried out after the butyrate has been converted into the corresponding butanol or acyl derivative. When both stereoisomeric forms of the butanol or the acyl derivatives are isolated, they are indicated as α- and β- forms, the α-form being the one derived from the erythro-3-aminobutyrates and the β-form being the one derived from the threo-aminobutyrates. When the steric conformation of the aminobutyrates has not been established, the final isomeric butanols and the corresponding acyl derivatives have been assigned the α- or β- form depending on the nuclear magnetic resonance (n m r) chemical shift, expressed in τ units, due to the hydrogen atoms of the $C_4$-methyl group. The isomer which exhibits the higher value of the chemical shift is assigned the α-form.

The separation of the stereoisomers is carried out using known methods and includes fractional crystallization and column chromatography. From each of the α- and β-stereoisomeric forms, which in turn are racemic mixtures, the optically active isomers may subsequently be isolated. For this purpose, usual procedures may be utilized such as, for example, fractional crystallization of salts of the 3-amino-1-butanols or their acyl derivatives with optically active acids.

The arylcrotonate starting materials are prepared by the method of Bellasio et al., (Farmaco, Ed. Sci. 1970, 25(6), 409) or in a more convenient way via a Wittig reaction between alkyl esters of arylglyoxylic acids and ethyltriphenylphosphonium halides in the presence of phenyllithium:

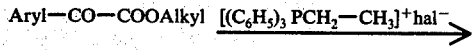

-continued

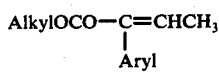

The compounds of the present invention display marked coronary dilating activity. In experiments carried out in anesthesized dogs, amounts from about 0.2 to about 2 mg/kg i.v. were highly effective in increasing the coronary blood flow without affecting the other cirulatory parameters such as the systemic blood pressure and the heart rate. The $LD_{50}$ values are generally higher than 500 mg/kg per os. Representative of such activity, the compound of Example 13, at doses of 0.2, 0.5 and 1 mg/kg, increased the coronary blood flow by 40, 100 and 120%, respectively. The compounds of Examples 2, 6, 7, 10 and 18 have substantially the same level of activity.

The inventive compounds can also be administered by mouth. For oral administration, the active substances are compounded into suitable pharmaceutical forms such as, for example, tablets or capsules which may contain the usual excipients such as, for example, starch, gums, sugars, fatty acids and other pharmaceutical carriers. The dosage range is from about 0.5 to about 10 mg/kg of body weight per day, preferably administered in divided doses.

DESCRIPTION OF THE PREFERRED EMBODIMENTS

The following non-limitative examples provide additional embodiments illustrative of the preparation and best mode of carrying out the present invention.

EXAMPLE 1

Ethyl 2-(3,4-dichlorophenyl)-3-dimethylaminobutyrate

In a Parr bomb containing 45 g. of ethyl 2-(3,4-dichlorophenyl)crotonate in 250 ml. of ethanol add 100 ml. of aqueous 33 percent (w/v) dimethylamine and 0.8 ml. of acetic acid. The mixture is maintained with stirring at 50° C for 10 hours, then the solvent is evaporated in vacuo and the residue, after suspension in water, is extracted several times with ether. After evaporation of the dried organic layer, 60 g. of the title compound is obtained which boils at 124° C/0.2 mm Hg. The product is an approximately 50:50 mixture of the two stereoisomers Pursuant to the above procedure, the following compounds are similarly prepared from the analogous 2-(3,4-dimethoxyphenyl) and the 2-phenyl starting materials:
ethyl 2-(3,4-dimethoxyphenyl)-3-dimethylaminobutyrate oxalate, m.p. 157°-160° C.
ethyl 2-phenyl-3-dimethylaminobutyrate oxalate, m.p. 128°-30° C.

EXAMPLE 2

2-(3,4-Dichlorophenyl)-3-dimethylamino-1-butanol

To a suspension of 10 g. of lithium aluminum hydride in 300 ml. of diethyl ether, 18.7 g. of ethyl 2-(3,4-dichlorophenyl)-3-dimethylaminobutyrate is added dropwise with stirring. The mixture is refluxed for 40–45 hours and after cooling with an ice bath, 50 ml. of water is added very slowly. After filtering off and thoroughly washing out the inorganic salts, the dried organic filtrate is evaporated and the residue is distilled in vacuo at 115° C/0.4 mm Hg to yield 13 g. of the title compound. The hydrochloride salt melts at 188°-190° C.

EXAMPLE 3

α-2-(3,4-Dichlorophenyl)-3-(dimethylamino)-butyl cinnamate hydrochloride

β-2-(3,4-Dichlorophenyl)-3-(dimethylamino)-butyl cinnamate hydrochloride

To a solution of 19 g. of ethyl 2-(3,4-dichlorophenyl)-3-dimethylamino-1-butanol and 14.4 g. of triethylamine in 75 ml. of dioxane, 24 g. of cinnamoyl chloride in 150 ml. of dioxane is added and the mixture if refluxed for two hours. After standing over night, the triethylamine hydrochloride is filtered off and the solution is concentrated to a small volume. An ethyl ether solution of hydrogen chloride is then added. The crude product which precipitates is dissolved in 30 ml. of hot isopropanol and, after standing for 10 days in a refrigerator, 6.2 g. of a solid is recovered by filtration. A further crystallization of the solid from dioxane gives 3 g. of the pure β-stereoisomer of 2-(3,4-dichlorophenyl)-3-(dimethylamino)butyl cinnamate hydrochloride which melts at 173° C.

The mother liquor of the first crystallization from isopropanol is evaporated to dryness and the residue taken up twice with 200 ml. of ethyl ether. After decantation, the solid is recovered by filtration and then dissolved in 100 ml. of hot dioxane.

On addition of 100 ml. of ethyl ether to the cooled dioxane solution, a crystalline solid precipitates which in turn is again dissolved in 70 ml. of isopropanol and reprecipitated with ethyl ether to give a yield of 11.3 g. of the hydrochloride of the α-stereoisomer of 2-(3,4-dichlorophenyl)-3-(dimethylamino)butyl cinnamate which melts at 110° C.

EXAMPLE 4

2-Phenyl-3-dimethylamino-1-butanol

The title compound is prepared according to the procedure of Example 2, from ethyl 2-phenyl-3-dimethylaminobutyrate and lithium aluminum hydride. B.p. 126°-129° C/0.2 mm Hg.

EXAMPLE 5

2-(3,4-Dimethoxyphenyl)-3-dimethylamino-1-butanol

The title compound is prepared according to the procedure of Example 2, from ethyl 2-(3,4-dimethoxyphenyl)-butyrate and lithium aluminum hydride. B.p. 140° C/0.2 mm Hg.

EXAMPLE 6

β-2-Phenyl-3-(dimethylamino)butyl (p-isobutylphenyl)acetate dimaleate

The title compound is prepared from ethyl 2-phenyl-3-dimethylaminobutyrate and lithium aluminum hydride according to the procedure of Example 2, followed by reaction with (p-isobutylphenyl)acetyl chloride according to the procedure of Example 3. Addition of maleic acid instead of hydrogen chloride and fractional crystallization from isopropanol gives the β-isomer as the main product. It melts at 105°-106° C.

EXAMPLE 7

β-Phenyl-3-(dimethylamino)butyl cinnamate hydrochloride

The title compound is prepared from ethyl 2-phenyl-3-dimethylaminobutyrate and lithium aluminum hydride according to the procedure of Example 2, followed by reaction with cinnamoyl chloride according to the procedure of Example 3. Fractional crystallization from isopropanol gives the β-isomer as the main product. It melts at 188°–190° C.

EXAMPLE 8

α-2-Phenyl-3-(dimethylamino)butyl 3,4,5-trimethoxybenzoate hydrochloride

The title compound is prepared from ethyl 2-phenyl-3-dimethylaminobutyrate and lithium aluminum hydride according to the procedure of Example 2 followed by reaction with 3,4,5-trimethoxybenzoyl chloride according to the procedure of Example 3. Fractional crystallization from isopropanol gives the β-isomer as the main product. M.p. 202°–204° C.

EXAMPLE 9

β-Phenyl-3-(dimethylamino)butyl 3,4,5-trimethoxybenzoate hydrochloride

The title compound is prepared from ethyl 2-phenyl-3-dimethylaminobutyrate and lithium aluminum hydride according to the procedure of Example 2 followed by reaction with 3,4,5-trimethoxybenzoyl chloride according to the procedure of Example 3. Fractional crystallization from isopropanol gives the β-isomer as the main product. It melts at 165°–166° C.

EXAMPLE 10

β-2-(3,4-Dimethoxyphenyl)-3-(dimethylamino)-butyl 3,4,5-trimethoxybenzoate hydrochloride The title compound is prepared from 2-(3,4-dimethoxy)phenyl-3-dimethylamino-1-butanol and 3,4,5-trimethoxybenzoyl chloride according to the procedure of Example 3. Fractional crystallization from ethanol gives the β-isomer as the main product. It melts at 182°–183° C.

EXAMPLE 11

α-2-(3,4-Dimethoxyphenyl)-3-(dimethylamino)-butyl (p-isobutylphenyl)acetate picrate The title compound is prepared from 2-(3,4-dimethoxyphenyl)-3-dimethylamino-1-butanol and (p-isobutylphenyl)acetyl chloride according to the procedure of Example 3. Addition of picric acid instead of hydrogen chloride and fractional crystallization from isopropanol gives the α-isomer as the main product. It melts at 127°–129° C.

EXAMPLE 12

α-2-(3,4-Dichlorophenyl)-3-(dimethylamino)-butyl (p-isobutylphenyl)acetate hydrochloride The title compound is prepared from 2-(3,4-dichlorophenyl)-3-dimethylamino-1-butanol and (p-isobutylphenyl)acetyl chloride according to the procedure of Example 3. Fractional crystallization from isopropanol gives the α-isomer as the main product. The hydrochloride melts at 188°–190° C.

EXAMPLE 13

α-2-(3,4-Dichlorophenyl)-3-(dimethylamino)-butyl 3,4,5-trimethoxybenzoate hydrochloride The title compound is prepared from 2-(3,4-dichlorophenyl)-3-dimethylamino-1-butanol and 3,4,5-trimethoxybenzoyl chloride according to the procedure of Example 3. Fractional crystallization from isopropanol gives the α-isomer as the main product. The hydrochloride melts at 204°–205° C.

EXAMPLE 14

2-(3,4-Dimethoxyphenyl)-3-(benzylamino)-1-butanol hydrochloride

The title compound is prepared from ethyl 2-(3,4-dimethoxyphenyl)-3-benzylaminobutyrate and lithium aluminum hydride according to the procedure of Example 2. M.p. 180°–182° C from diethyl ether. The starting butyrate is prepared according to the procedure of Example 1 from ethyl α-(3,4-dimethoxyphenyl)crotonate and benzylamine and is used in the crude state.

EXAMPLE 15

2-Phenyl-3-(3,4-dimethoxyphenethylamino)-1-butanol hydrochloride

The title compound is prepared from ethyl 2-phenyl-3-(3,4-dimethoxyphenethylamino)butyrate and lithium aluminum hydride according to the procedure of Example 2. M.p. 157°–158° C from isopropanol. The starting butyrate is prepared according to the procedure of Example 1 from ethyl α-phenylcrotonate and 3,4-dimethoxyphenethylamine and is used in the crude state.

EXAMPLE 16

2-(3,4-Dimethoxyphenyl)-3-(3,4-dimethoxyphenethylamino)-1-butanol hydrochloride

The title compound is prepared from ethyl 2-(3,4-dimethoxyphenyl)-3-(3,4-dimethoxyphenethylamino)-butyrate and lithium aluminum hydride according to the procedure of Example 2. M.p. 175°–176° C from isopropanol. The starting butyrate is prepared according to the procedure of Example 1 from α-(3,4-dimethoxyphenyl)crotonate and 3,4-dimethoxyphenethylamine and is used in the crude state.

EXAMPLE 17

β-2-(3,4-Dichlorophenyl)-3-benzylamino-1-butanol hydrochloride

The title compound is prepared from ethyl threo-2-(3,4-dichlorophenyl)-3-benzylaminobutyrate and lithium aluminum hydride according to the procedure of Example 2. M.p. 214°–215° C from ethanol.

EXAMPLE 18

β-2-(3,4-Dichlorophenyl)-3-(dimethylamino)-butyl phenylcarbamate hydrochloride

The compound is prepared by adding 4.5 g. of phenylisocyanate to 10 g. of 2-(3,4-dichlorophenyl)-3-dimethylamino-1-butanol in 100 ml. of benzene at room temperature. Evaporation of the solution after standing over night gives a residue which is dissolved in ethyl ether and then transformed to the hydrochloride by addition of dry HCl. Fractional crystallization of the precipitate from isopropanol gives the β-isomer as the main product. M.p. 205°–207° C.

EXAMPLE 19

α-2-Phenyl-3-benzylamino-1-butanol hydrochloride

The title compound is prepared from ethyl erythro-2-phenyl-3-benzylaminobutyrate and lithium aluminum hydride according to the procedure of Example 2. It melts at 220°–222° C. The free base boils at 140° C/0.8 mm Hg.

EXAMPLE 20

2-(3,4-Dichlorophenyl)-3-amino-1-butanol

The compound is prepared according to the procedure described in Example 2, using as starting material 5.5 g. of ethyl 2-(3,4-dichlorophenyl)-3-aminobutyrate. Yield 3.75 g.; boiling point 125° C/0.2 mm Hg. The hydrochloride melts at 157°–160° C.

EXAMPLE 21

2-(3,4-Dimethoxyphenyl)-3-amino-1-butanol

The compound is prepared according to the procedure of Example 20, using as starting material ethyl 2-(3,4-dimethoxyphenyl)-3-aminobutyrate. B.p. 185°–190° C/0.2 mm Hg.

EXAMPLE 22

2-(1-Naphthyl)-3-amino-1-butanol hydrochloride

The compound is prepared according to the procedure of Example 20, using as starting material ethyl 2-(1-naphthyl)-3-aminobutyrate. M.p. 253°–258° C. from ethanol.

EXAMPLE 23

Ethyl 2-Aryl-3-aminobutyrates

These compounds are prepared by treating in a Parr bomb the corresponding ethyl 2-arylcrotonates with an ethanol solution saturated with ammonia in the presence of cupric acetate and acetic acid as a catalyst. The reaction is carried out under a nitrogen atmosphere by treating the mixture for 8–30 hours at 40° C. The crude end compounds are recovered by evaporation of the solvent. The erythro and threo isomers are isolated by fractional crystallization of the corresponding acid salts as described by Bellasio et al., Farmaco, Ed. Sci. 1970, 25 (6), 347, 409.

a. Ethyl 2-phenyl-3-aminobutyrates; b.p. 125° /0.1 mm Hg.
b. Ethyl threo-2-phenyl-3-aminobutyrate oxalate; m.p. 150°–152° C
c. Ethyl erythro-2-phenyl-3-aminobutyrate oxalate; m.p. 158°–160° C
d. Ethyl 2-(3,4-dichlorophenyl)-3-aminobutyrate hydrochloride; m.p. 158°–160° C
e. Ethyl threo-2-(3,4-dichlorophenyl)-3-aminobutyrate hydrochloride; m.p. 163°–165° C
f. Ethyl erythro-2-(3,4-dichlorophenyl)-3-aminobutyrate hydrochloride; m.p. 198°–200° C
g. Ethyl 2-(3,4-dimethoxyphenyl)-3-aminobutyrate hydrochloride; m.p. 167°–180° C
h. Ethyl 2-(1-naphthyl)-3-aminobutyrate; b.p. 140/0.2 mm Hg.

The ethyl 2-arylcrotonate starting materials are prepared as follows.

EXAMPLE 24

Ethyl α-(3,4-dimethoxyphenyl)crotonate

To a diethyl ether solution of ethylidenetriphenylphosphorane prepared in the usual way from 800 g. of ethyltriphenylphosphonium bromide, 400 g. of ethyl 3,4-dimethoxyphenylglyoxylate in 600 ml. of ether are added dropwise. After refluxing for 4–5 hours, the solvent is evaporated and substituted with tetrahydrofuran. The mixture is then heated for 36 hours and then evaporated to dryness and the residue is extracted with diethyl ether in a Soxhlet apparatus giving 150 g. of the title compound. Pursuant to this procedure, the following other α-arylcrotonate starting materials are prepared:

ethyl α-(3,4-dichlorophenyl)-crotonate
ethyl α-(phenyl)-crotonate
ethyl α-(1-naphthyl)-crotonate

We claim:
1. The compound β-2-(3,4-dimethoxyphenyl)-3-(dimethylamino)butyl 3,4,5-trimethoxybenzoate hydrochloride.
2. The compound α-2-(3,4-dichlorophenyl)-3-(dimethylamino)butyl 3,4,5-trimethoxybenzoate hydrochloride.

* * * * *